United States Patent
Biernat et al.

(10) Patent No.: US 8,123,353 B2
(45) Date of Patent: Feb. 28, 2012

(54) OPHTHALMOLOGIC APPARATUS AND METHOD FOR THE OBSERVATION, EXAMINATION, DIAGNOSIS, AND/OR TREATMENT OF AN EYE

(75) Inventors: Detlef Biernat, Jena (DE); Daniel Bublitz, Jena (DE); Andreas Brodschelm, Munich (DE); Thomas Mohr, Jena (DE); Stefan Richter, Jena (DE)

(73) Assignee: Carl Zeiss Meditec AG, Jena, DE (US)

( * ) Notice: Subject to any disclaimer, the term of this patent is extended or adjusted under 35 U.S.C. 154(b) by 0 days.

(21) Appl. No.: 12/919,478

(22) PCT Filed: Feb. 25, 2009

(86) PCT No.: PCT/EP2009/001318
§ 371 (c)(1), (2), (4) Date: Dec. 15, 2010

(87) PCT Pub. No.: WO2009/106298
PCT Pub. Date: Sep. 3, 2009

(65) Prior Publication Data
US 2011/0116040 A1      May 19, 2011

(30) Foreign Application Priority Data
Feb. 28, 2008   (DE) .................... 10 2008 011 836

(51) Int. Cl.
*A61B 3/10*     (2006.01)
*A61B 3/14*     (2006.01)
(52) U.S. Cl. ................. 351/205; 351/210; 351/214
(58) Field of Classification Search .......... 351/205, 351/200, 206, 210, 213–215, 221
See application file for complete search history.

(56) References Cited

U.S. PATENT DOCUMENTS

| 4,730,910 | A |   | 3/1988  | Humphrey |
|-----------|---|---|---------|----------|
| 4,968,130 | A |   | 11/1990 | Hideshima et al. |
| 5,279,298 | A | * | 1/1994  | Flower .................... 600/321 |
| 5,822,446 | A | * | 10/1998 | Kato ....................... 382/128 |
| 6,337,920 | B1|   | 1/2002  | Muehlhoff |
| 7,134,754 | B2|   | 11/2006 | Kerr et al. |
| 7,198,367 | B2|   | 4/2007  | Akita et al. |
| 7,500,753 | B2|   | 3/2009  | Mueller et al. |
| 7,810,929 | B2|   | 10/2010 | Mueller et al. |

(Continued)

FOREIGN PATENT DOCUMENTS

DE    38 36 860 C3    5/1989

(Continued)

*Primary Examiner* — Dawayne Pinkney
(74) *Attorney, Agent, or Firm* — Patterson Thuente Christensen Pedersen, P.A.

(57) ABSTRACT

An ophthalmologic apparatus and a method for the contactless observation, examination, treatment, and/or diagnosis of an eye. The apparatus is structurally based on a fundus camera or an ophthalmoscope. An illumination beam path extends from a first illumination source to the eye and is fitted with a perforated mirror and imaging optics, and an observation beam path extends from the eye to a detector via the imaging optics and through the perforated mirror. The arrangement additionally comprises a beam path for scanning illumination which extends from a second illumination source to the eye and is fitted with a scanning unit, a lens, and a beam splitter in addition to the imaging optics. The scanning unit that is arranged in the beam path for scanning illumination is designed as (an) electrostatically or/and galvanometrically driven bidirectional or unidirectional tilting mirror(s).

30 Claims, 4 Drawing Sheets

U.S. PATENT DOCUMENTS

| | | |
|---|---|---|
| 2002/0058874 A1 | 5/2002 | Ono et al. |
| 2004/0156016 A1* | 8/2004 | Kerr et al. ..................... 351/206 |
| 2006/0187462 A1 | 8/2006 | Srinivasan et al. |
| 2006/0203194 A1 | 9/2006 | Suzuki |
| 2007/0188707 A1 | 8/2007 | Nanjo |
| 2007/0252951 A1* | 11/2007 | Hammer et al. ............. 351/221 |
| 2007/0291277 A1 | 12/2007 | Everett et al. |
| 2008/0088795 A1* | 4/2008 | Goldstein et al. ............. 351/206 |
| 2010/0073634 A1* | 3/2010 | Ferguson et al. ............. 351/206 |

FOREIGN PATENT DOCUMENTS

| | | |
|---|---|---|
| EP | 0 392 744 A1 | 10/1990 |
| EP | 0 659 383 A2 | 6/1995 |
| EP | 1 308 124 A2 | 5/2003 |
| WO | WO 97/37584 | 10/1997 |
| WO | WO 2004/043234 A2 | 5/2004 |
| WO | WO 2006/052479 A2 | 5/2006 |
| WO | WO 2007/035855 A2 | 3/2007 |

* cited by examiner

Figure 1

PRIOR ART

OPHTHALMOLOGIC APPARATUS AND METHOD FOR THE OBSERVATION, EXAMINATION, DIAGNOSIS, AND/OR TREATMENT OF AN EYE

PRIORITY CLAIM

The present application is a National Phase entry of PCT Application No. PCT/EP2009/001318, filed Feb. 25, 2009, which claims priority from German Application Number 102008011836.2, filed Feb. 28, 2008, the disclosures of which are hereby incorporated by reference herein in their entirety.

FIELD OF THE INVENTION

The invention relates to an ophthalmological device and method for non-contact observation, examination, therapy, and/or diagnosis of an eye. In its design, the device is based on a fundus camera and/or an ophthalmoscope.

BACKGROUND OF THE INVENTION

Images of the topology of the eyeground (retina or fundus) are important for the diagnosis of many eye diseases. Many of the diseases of the retina can be examined more precisely with the accurate use of diagnostic lasers and treated with the precisely accurate application of therapy lasers.

In the prior art, numerous and diverse solutions are known for the observation, diagnosis, and therapy of the eye. Therein, the required images are produced, e.g., with hand-held ophthalmoscopes, slit lamps, fundus cameras, or laser scanning ophthalmoscopes.

Fundus cameras are one of the most important diagnostic instruments in ophthalmology. With their help, it is possible to map wide field images of the eye fundus and deduce diagnoses therefrom.

In [1], R. F. Spaide describes special embodiments, with which it is possible to apply functional types of diagnoses beyond the mere evaluation of the RGB image (red, green, blue).

For example, in U.S. Pat. No. 7,134,754 B2, a retinal function camera is described, which includes two laser light sources with different wavelengths. Thereby, the wavelength bands are selected in such a way that the absorptivity of light of the first wavelength band is greater with oxygenated blood and the absorptivity of light of the second wavelength is greater with deoxygenated blood; as a result, respective images can be produced and analyzed.

Hence it is possible to diagnose even early stages of macular atrophy, which causes age-related loss of photoreceptor cells and retinal pigment epithelium and leads to gradual loss of detailed central vision.

However, with the described solution, the forming of choroidal neovascularization in early stages can also be detected. These small, new, anomalous blood vessels grow and proliferate from the choroid layer and can cause acute loss of vision if blood collects in or below the retina. The diseased spots made visible with the described solution can be treated either with photo coagulation of by application of photodynamic therapy.

A fundus camera, which also includes the use of two laser light sources with different wavelengths, is described in U.S. Pat. No. 7,198,367 B2. Thereby, however, the wavelength bands are chosen in such a way that fluorescence images of the fundus can be mapped and analyzed in the visible as well as the infrared range.

However, the currently known functional diagnoses with a fundus camera are still based on the principles of the wide field illumination. A more complex diagnosis, which takes place in individual spots on the retina, such as perimetry, optical coherence tomography or a precisely accurate therapy through coagulation, is still not possible with said system.

Furthermore, laser scanning ophthalmoscopes have also become established in ophthalmology. Hereby, a laser beam is usually mapped confocally onto the retina via a mechanical scanner, e.g., a galvanometer scanner or a polygon mirror. The light returned from the retina in the mapped spot is detected by a sensor inside the device.

The information about the topography of the retina is gathered through scanning with the help of the scanner. With laser scanning ophthalmoscopes it is possible to perform a precisely accurate therapy or diagnosis of the retina. In a conventional laser scanning ophthalmoscope, the laser serves as light source for imaging as well as for diagnosis and/or therapy.

However, since the eye of a patient can move during observation relative to the ophthalmoscope, it is necessary to constantly observe the topography of the eye fundus. For that reason, resonantly driven scanners, which continuously scan the retina, are used in all known laser scanning ophthalmoscopes. A precisely accurate therapy or diagnosis is only possible when the scanner is aligned in such a way that the laser point covers exactly the desired spot on the retina. Therefore, an elaborate synchronization between scanner and the therapy or diagnostic laser is required.

In order to avoid exceeding the maximum admissible impulse energies during treatment, it is necessary to control the resting time of the scanning laser beam, depending on its intensity, through an elaborate positioning device and an intensity monitor. For example, in WO 2004/043234 A1, an optimized laser scanning ophthalmoscope is described, wherein a confocal laser scanning laser ophthalmoscope and external laser sources are combined in order to simultaneously observe and treat the same spot on the retina.

Thereto, EP 1 308 124 A2 describes a lens system for the use with a laser scanning ophthalmoscope. The described lens system realizes a very broad wide field, so that areas of the eye can be examined by the laser scanning ophthalmoscope which are ordinarily inaccessible.

A further laser scanning ophthalmoscope is described in U.S. Pat. No. 6,337,920 B1. The laser scanning ophthalmoscope (LSO), which consists of a laser-beam producing laser light source, a first scanning device for producing an oscillating beam deflection in a first direction, and a second scanning device for producing an oscillating beam deflection in a second direction, also contains detection devices for detecting the light reflected from the eye.

From the fundus image produced by a first scan of the retina, sub-areas of the fundus can be selected, onto which a second scan can be focused, particularly, refined. Thereby, the individual scanning devices are independently swivel-mounted via drive motors controlled by an activation device.

DE 38 36 860 C2 describes an ophthalmological device with laser beam scanning. This solution also uses two wavelengths. While one laser beam is utilized for coagulation/excitation of the fundus, the other laser beam is used for scanning imaging of the fundus, whereby both laser beams are utilized parallel and simultaneously. This solution provides an ophthalmological device with laser beam scanning with which a designated spot of the fundus can be marked on the screen and an adequate image of said spot produced.

A third option for simultaneous imaging of the eye fundus and application of therapy lasers on the retina consists of the use of slit lamps. However, in order to position said slit lamps precisely, a fixation of the eye is required. A fixation is usually achieved through a contact glass. The contact glass also serves as compensation for the refractive power of the eye.

Thereby, it is disadvantageous that the laser coagulation with a slit lamp requires a contact glass, and its reproducibility is extremely low.

Furthermore, the accuracy of positioning the laser spot on the retina depends greatly on the operator since a precisely accurate therapy or diagnosis is only possible if the scanner is aligned in such a way that the laser spot covers exactly the desired spot on the retina. Thereto, elaborate synchronization between scanner and the therapy or diagnostic laser is absolutely necessary. In order to avoid exceeding the maximum admissible impulse energies during treatment, it is necessary to control the resting time of the scanning laser beam on the interesting spot, depending on its intensity, through elaborate positioning devices and an intensity monitor.

The method as well as the respective device described in WO 2007/035855 A2 are based on the principle of a slit lamp, which was expanded with a scan unit in order to execute a pattern-assisted laser coagulation on the retina. This, however, requires the positioning of a contact glass on the patient's eye, with which the refractive power of the eye is compensated and/or a beam shaping of the laser for coagulation is performed. In addition, only a local therapy of the retina is possible due to the very small observation area when compared with the fundus camera. This is caused by the basic design of a slit lamp. In order to treat larger areas of the retina, the eye of the patient must be moved or special contact glasses must also be applied.

Moreover, it is not possible to perform a fundus image-based positioning for the coagulation laser as well as document the set coagulation points. Diagnostic procedures, such as perimetry, fluorescence imaging, spectroscopic analyses, or optical coherence tomography are also impossible.

LITERATURE

[1] Spaide, R. F., "Fundus autofluorescence and age-related macular degeneration," Ophthalmology 110(2), February 2003, p. 392-399

SUMMARY OF THE INVENTION

The invention herein is based on the task of developing an ophthalmological device and method for non-contact observation, examination, diagnosis, and/or therapy of an eye. Thereby, independently from diagnosis and/or therapy, observation and/or imaging should be possible with said device which, preferably, is based on the design of a fundus camera and/or an ophthalmoscope. Particularly, the solution developed allows for high reproducibility and automatic documentation from the examination and diagnosis all the way through the therapy process.

The ophthalmological device for observation, examination, diagnosis, and/or therapy of an eye, according to the invention, includes an illumination beam path which, originating from a first illumination source, leads to the eye, and which also exhibits a perforated mirror and imaging optics as well as an observation beam path, which, originating from the eye, leads via the imaging optics and through the perforated mirror to a detector. In addition, the ophthalmological device exhibits a beam path for the scanning illumination, which, originating from a second illumination source, leads to the eye, and, in addition to the imaging optics, includes a scan unit, a lens, and a beam splitter. Thereby, the imaging optics, as well as the entire beam path, are designed in such a way that they are free of internal reflections. The scan unit, positioned in the beam path for the scanning illumination, is designed as an electrostatically and/or galvanometrically driven bidirectionally adjustable mirror or as two electrostatically and/or galvanometrically driven unidirectionally adjustable mirrors. If two electrostatically and/or galvanometrically driven unidirectionally adjustable mirrors are used, a preferably intermediate imaging of the mirrors onto each other takes place.

In the method for observation, examination, diagnosis, and/or therapy of an eye, according to the invention, the eye is illuminated independently for observation and examination with a first illumination source and for diagnosis and/or therapy with a second illumination source. The light from the eye, initiated by the first, as well as the second illumination source, is mapped, recorded, processed, analyzed, documented and stored via imaging optics and through a perforated mirror to a detector.

In a conventional laser scanning ophthalmoscope, the laser is used, e.g., as light source for imaging as well as diagnosis/therapy. Thereto, the field of view on the retina is scanned with a laser via a resonance-driven scanner (galvanometer scanner, polygon). By contrast, imaging in our claimed solution takes places through a wide field illumination and a camera, whereby all image information is available within the course of the temporal resolution of the camera.

With the solution, according to the invention, imaging takes place through a wide field illumination and a camera, whereby all image information is available within the course of the temporal resolution of the camera. Therefore, imaging is uncoupled from diagnosis and/or therapy.

As a result, diagnosis and therapy can be performed not only at discreet points in time when the laser spot within the grid for imaging has reached the position to be treated and/or diagnosed, but at any given point in time.

The restrictions regarding the setting time of the laser scanner are only limited by the mirror's moment of inertia as well as the electrostatic and/or galvanometric and mechanical setting forces. Since it is possible to dispense with an elaborate synchronization of the laser light source with the scan unit, this potential source of error is avoided.

The problem, which is solved with the suggested solution, lies in the attempt to combine the image of the eye fundus with the precisely accurate application of therapy and/or diagnostic lasers. This is necessary because the location of the application of the therapy and/or diagnostic laser must be determined and monitored during application. Furthermore, a thorough, precisely accurate possibility for diagnosis could be sensible even during the examination of the topology of the eye fundus in order to examine, e.g., tumorous tissue more thoroughly.

Thereby, said diagnostic and/or therapy option is possible without fixation of the eye. Due to the non-contact approach, the special risk of infections is diminished. For monitoring of the position of the therapy and/or diagnosis spot on the retina, an aiming beam can be used, which indicates said position.

Moreover, it is important that in the combined application of therapy and diagnostic laser and a fundus camera, all existing tools and adjustment aids, such as positioning aid, focusing aid, and retaining aid of the fundus camera are available for easy and quick operation.

Due to the optical designs of fundus cameras, a simple coupling of a laser scanner in the beam path of a fundus camera is not readily possible. The laser scanner must be coupled on the optical axis in order to ensure a uniform imaging of the diagnostic and/or therapy laser in all areas of the retina. Thereby, however, the problem of returning reflections in the center of the inserted lenses is unavoidable.

Due to the low intensity of the signal returned from the retina, said returning reflection significantly outshines the useful signal.

The invention herein presents a solution in the form of an ophthalmological device and method for non-contact observation, examination, diagnosis, and/or therapy of an eye. Said device, which, preferably, is based in its design on a fundus camera and/or an ophthalmoscope, allows for observation and/or imaging independently from a diagnosis and/or therapy. Therefore, it offers the possibility of executing numerous examinations, diagnoses, and even treatments of an eye with only one device. The high reproducibility and possibility of an automatic documentation from the examination and diagnosis all the way through the therapy process offer an additional essential advantage when compared to separate single devices.

BRIEF DESCRIPTION OF THE DRAWINGS

In the following, the solution, according to the invention, is described with relation to example embodiments.

DETAILED DESCRIPTION

Figure 1:
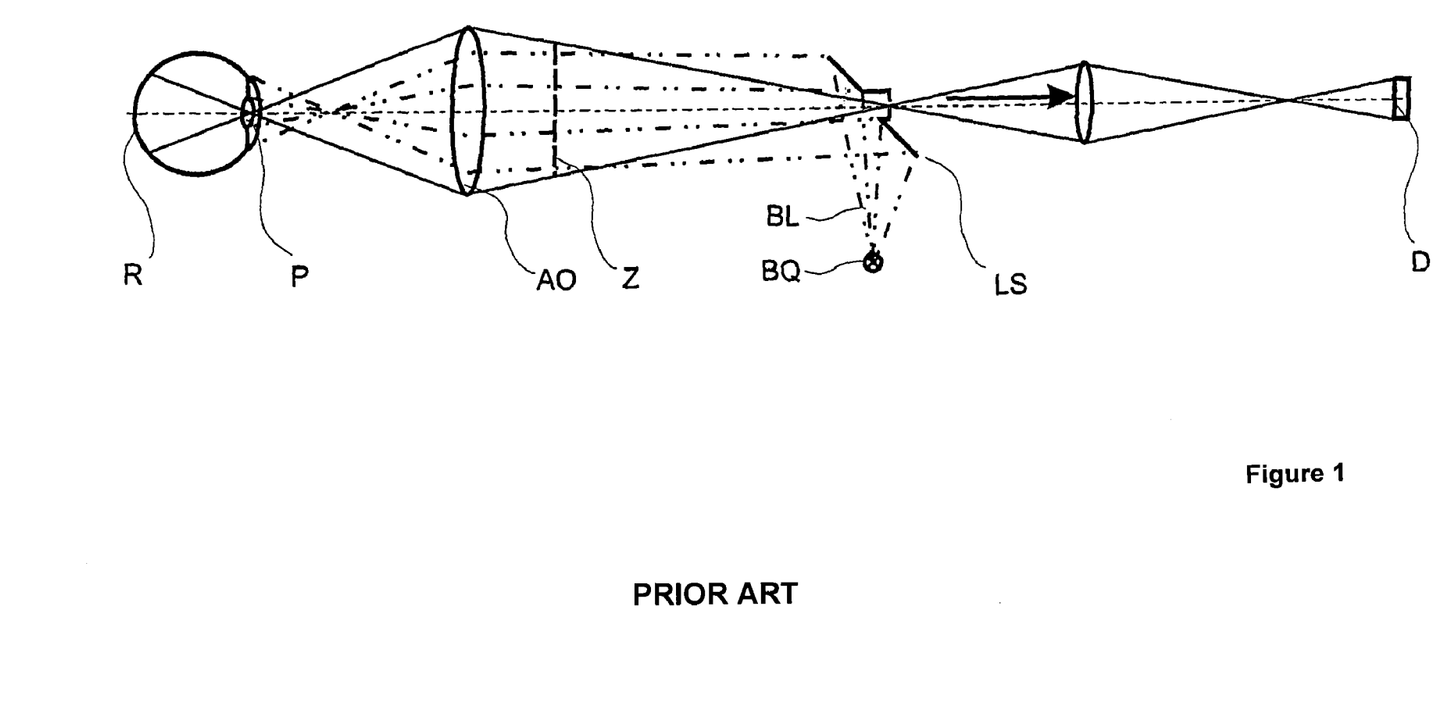
FIG. 1 is a schematic design of a fundus camera, according to prior art.

At first, and in order to better illustrate the suggested technical solution, prior art shall once more be described. Thereto, FIG. 1 shows the schematic design of a known fundus camera.

In a fundus camera, according to prior art, the illumination light BL, originating from an illumination source BQ, is mapped via a perforated mirror LS and imaging optics AO through the pupil P on the retina R of the eye. For the purpose of imaging, the light reflected from the retina R of the eye is mapped on a detector D through the pupil P of the eye via the imaging optics AO and through the perforated mirror LS. Thereby, an intermediate image Z is produced from the image of the retina R between imaging optics AO and perforated mirror LS and mapped through the aperture of the perforated mirror LS on the detector D in the form of a CCD camera.

Thereby, the illumination source produces white or infrared illumination light BL. The white light can either be emitted as continuous spectrum of conventional light sources, such as incandescent or halogen lamps, or mixed additively from several light sources (e.g., LED's) with spectrally different emissions (e.g., red, green, blue). Thereby, the illumination up to the eye lens is circular, leaving an unlit area through which the observation takes place.

As mentioned before, fundus cameras are one of the most important diagnostic instruments in ophthalmology. With their help, it is possible to map wide field images of the eye fundus and deduce diagnoses therefrom; however, a therapy through coagulation is not possible with said system.

The ophthalmological device for observation, examination, diagnosis, and/or therapy of an eye, according to the invention, includes an illumination beam path which, originating from a first illumination source, leads to the eye, and which also exhibits a perforated mirror and imaging optics as well as an observation beam path, which, originating from the eye, leads via the imaging optics and through the perforated mirror to a detector. In addition, the ophthalmological device exhibits a beam path for the scanning illumination, which, originating from a second illumination source, leads to the eye, and in addition to the imaging optics, includes a scan unit, a lens, and a beam splitter. Thereby, the imaging optics as well as the entire beam path are designed in such a way that they are free of internal reflections. The scan unit, positioned in the beam path for the scanning illumination, is designed as an electrostatically and/or galvanometrically driven bidirectionally adjustable mirror or as two electrostatically and/or galvanometrically driven unidirectionally adjustable mirrors. If two electrostatically and/or galvanometrically driven unidirectionally adjustable mirrors are used, a preferably intermediate imaging of the mirrors onto each other takes place.

The non-reflective realization of the entire beam path, and particularly the imaging optics, is a beneficial requirement for the functioning of the suggested technical solution since laser light reflected in the imaging lens would otherwise outshine the illumination used for imaging on the camera.

In one advantageous embodiment, the scan unit is designed according to MEMS technology and used for quasistatic operation. Thereby, the scan unit is capable of correcting lateral chromatic aberrations of the laser light source and/or the imaging optics. Thereby, said correction can, preferably, take place sequentially for different wavelengths. As a result, the position of the laser spot on the retina can be ensured with high reproducibility even with different laser wavelengths, especially in case of imaging aberrations. An additional option for correcting lateral chromatic aberrations of the imaging optics, and therefore the position of the laser spots of different wavelengths on the retina, is the use of a chromatically pre-corrected scan lens.

In another advantageous embodiment, at least one optical component is arranged adjustably for compensation of the defective vision of the eye. This can either be the lens positioned in the beam path for the scanning illumination or the existing collimation optics for the collimation of the laser on the scan unit. If several lasers are used, one or several collimation optics can thereby be adjustable.

Thereby, despite existing defective vision, a precisely accurate imaging of the laser spot on the retina is achieved. Thereto, the defective vision is preferably determined automatically by the ophthalmological device, similar to a fundus camera, with the values for sphere and, optionally, also cylinder and/or the higher-order aberrations, and taken into consideration for the imaging of the laser on the retina.

In an additional advantageous embodiment, the ophthalmological device exhibits means for depicting markers, as well as their variations with regard to form, wavelength, intensity as well as pulse duration and repetition. The light emitted by the illumination light sources is varied by an existing control unit with regard to form, wavelength, intensity, as well as pulse duration and repetition and their threshold values monitored.

If said threshold value is reached and/or other unforeseeable events occur, the diagnosis and/or therapy can be interrupted by the control unit through deactivation of the laser source via different safety-relevant components. In addition, the control unit also monitors the position of the laser spot on the retina in order to reduce possible cases of error to an infinitesimal minimum.

Thereby, the existing safety mechanisms must function with such accuracy and speed that especially the laser energy of aiming and therapy beam is reduced to a non-critical minimum in case of error. Furthermore, the existing safety mechanisms should function independently from each other as well as from possible operational errors by the operator.

The coupling of the scanning illumination is an additional important characteristic, according to the invention. Thereto, the existing dichroitic or polarization-dependent beam splitter in the beam path for the scanning illumination is arranged in such a way that the second illumination source is mapped centrally in the eye pupil via the scan unit and the lens.

Figure 2:
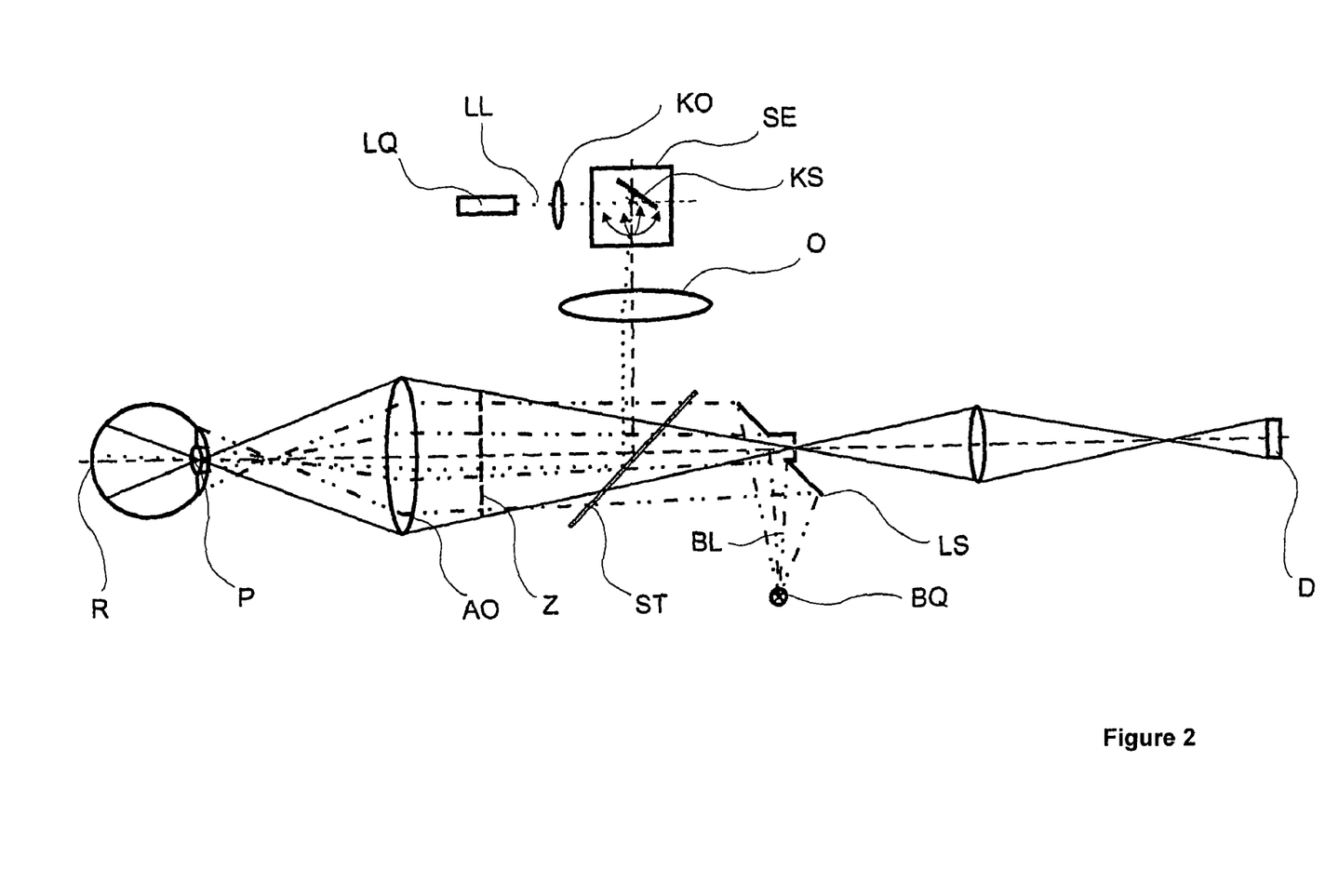
FIG. 2 is a schematic design of the ophthalmological device, according to an embodiment of the invention, with an adjustable mirror in the beam path for the scanning illumination.

Thereto, FIG. 2 shows the schematic design of the ophthalmological device, according to an embodiment of the invention, with a beam path for the scanning illumination of the eye. Once again, the illumination light BL, originating from an illumination source BQ, is mapped via a perforated mirror LS and imaging optics AO through the pupil P on the retina R of the eye, and for the purpose of imaging, the light reflected from the retina R of the eye is mapped on a detector D through the pupil P of the eye via the imaging optics AO while forming an intermediate image Z through the aperture of the perforated mirror LS. Commonly, a CCD camera or CMOS camera is once again used as detector D.

In addition to this known configuration, the ophthalmological device for observation, examination, diagnosis, and/or therapy of an eye, according to the invention, exhibits a beam path for the scanning illumination. The laser light LL from a laser source LQ is mapped on the retina R of the eye via collimation optics KO, scan unit SE with a single electrostatically and/or galvanometrically driven bidirectionally adjustable mirror KS, the lens O, and a beam splitter ST. Thereby, the dichroitic or polarization-dependent beam splitter ST is arranged in such a way that the laser light LL from the laser source LQ is mapped centrally in the pupil P of the eye.

A movement of the scan unit SE and the connected change of the deflection angle of the laser LL corresponds to a change of angle of the laser light LL in the pupil P of the eye and, therefore, to a change of position of the laser spot on the retina R. Thereby, the entry conditions of the laser into the eye, such as beam diameter and numerical aperture on the cornea, correspond to those at the exit of the contact glass of a slit lamp, under which the therapeutic procedure on the retina are executed. Contrarily, however, no contact glass is used for compensation of the refractive power of the eye.

The diagnostic and/or therapeutic use of a laser requires the free positionability of the laser spot on the retina R within the accessible scan area. Due to the imaging of the scan unit SE in the pupil P of the eye, it is advantageous to insert a single scan mirror. An electrostatically and/or galvanometrically driven bidirectionally adjustable mirror designed with MEMS technology can advantageously be tilted on two axis around a pivot point during the quasistatic operation.

Figure 3:
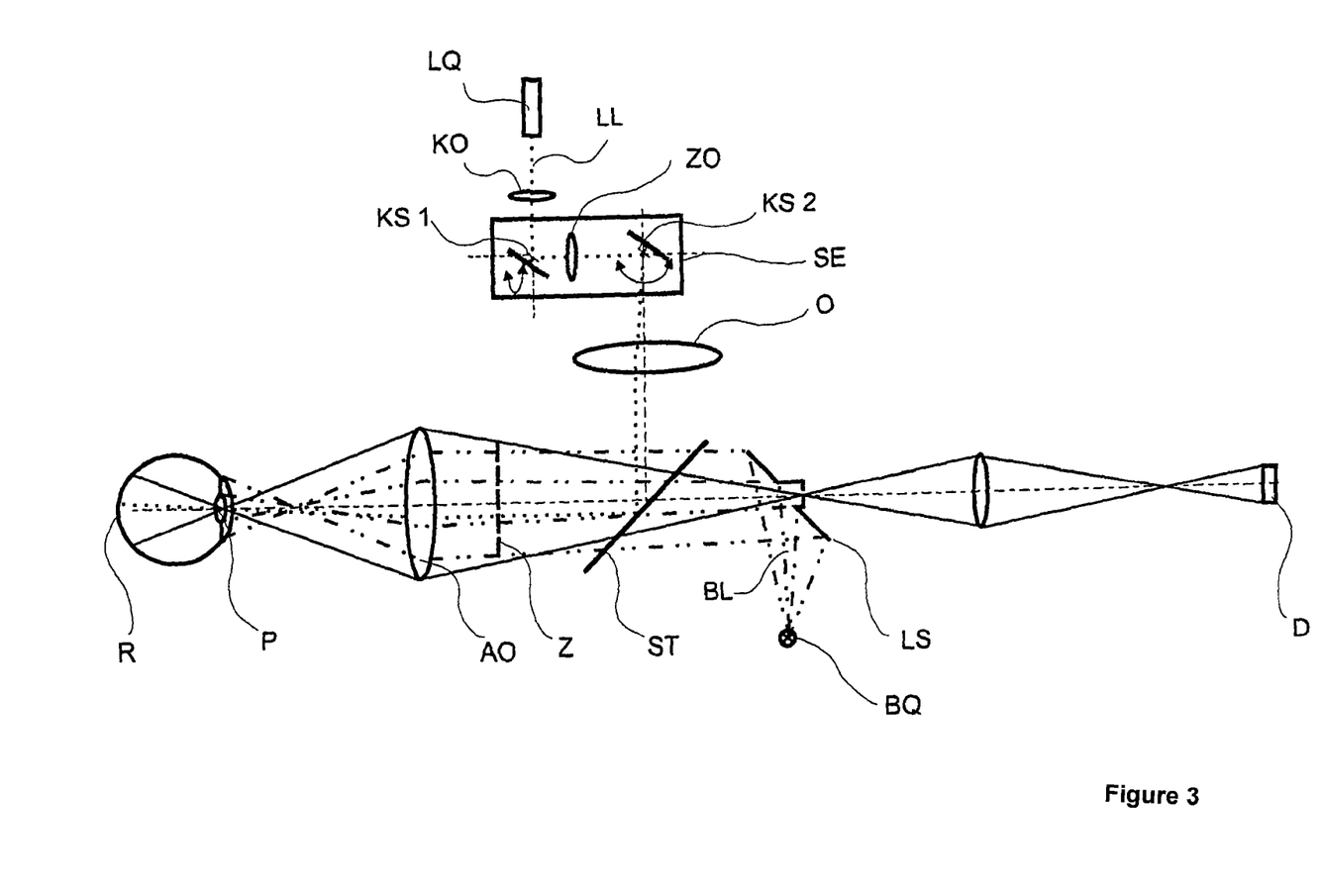
FIG. 3 is a schematic design of the ophthalmological device, according to an embodiment of the invention, with two adjustable mirrors in the beam path for the scanning illumination

Alternatively, as shown in FIG. 3, two unidirectionally adjustable mirrors can be used as scan unit SE. Thereby, it is advantageous to map the first adjustable mirror by means of intermediate optics on the second adjustable mirror, otherwise the subsequent image of the scan unit SE can at best only take place optimally for one of the mirrors.

In addition to the already described configuration (according to FIG. 2), the laser light LL of a laser source LQ is mapped on the retina R of the eye via collimation optics KO, a scan unit SE with two electrostatically and/or galvanometrically driven unidirectionally adjustable mirrors KS1 and KS2, the lens O, and a beam splitter ST.

Thereby, the dichroitic or polarization-dependent beam splitter ST is arranged in such a way that the laser light LL from the laser source LQ is mapped centrally in the pupil P of the eye. In order to map the first adjustable mirror KS1 onto the second adjustable mirror KS2, intermediate optics ZO are positioned between the two adjustable mirrors KS1 and KS2. Once again, the lens O, together with the beam splitter ST and the imaging optics AO, ensure the imaging of the scan unit SE into the pupil P of the eye.

With an electrostatic drive with direct current U, the adjustable mirrors possess the ability of tilting around an appropriately proportional angle $\theta$ and to keep such position until the value of the direct current U changes. This allows for a defined static positioning of the diffracted laser. In case of a galvanometric drive, the mirror is deflected statically around a current-proportional angle $\theta$ by means of direct current I, which runs through a coil connected with the mirror.

With the configuration, according to the invention, it is also possible to scanningly project several single light beams of the second illumination source simultaneously onto the eye. Thereto, the second illumination source includes several single light sources in the form of laser light sources as well as the beam splitter, required for possible simultaneous coupling of the single beams, and collimation optics, which in each case are positioned before the scan unit in the beam path for the scanning illumination.

Figure 4:
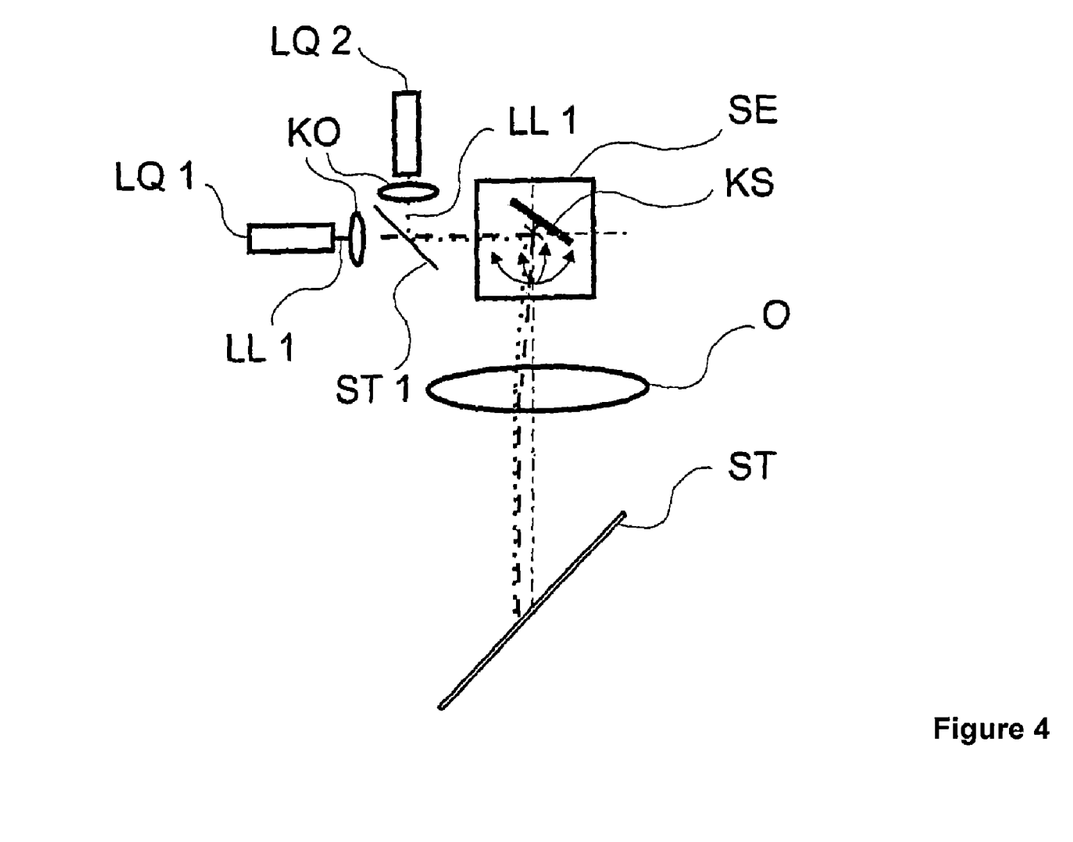
FIG. 4 is a variation for coupling two laser sources in the beam path for the scanning illumination.

Thereto, FIG. 4 shows a variation for coupling two laser sources in the beam path for the scanning illumination. Thereby, the laser source LQ consists of two laser sources LQ1 and LQ2, the collimated laser light beams LL1 and LL2 of which are coupled via the collimation optics KO1 and KO2 as well as the beam splitter ST1 before the scan unit SE and the lens O into the beam path for the scanning illumination. Thereby, the lens O, together with the beam splitter ST and the imaging optics AO, ensures the imaging of the scan unit SE, i.e. all laser light LL beams mapped simultaneously in that location, into the pupil P of the eye.

Thereby, the laser source LQ can also includes more than two laser sources LQ, the laser light beams LL of which are coupled via the collimation optics KO and beam splitter ST before the scan unit SE into the beam path for the scanning illumination.

For example, said variation of the configuration can, aside from a therapy or excitation beam for fluorescence examinations or the like, be used to project an additional aiming beam within the visible spectral range into the eye.

It has a beneficial effect that the light beams of both illumination sources are widened at the optical boundary layers of the eye, resulting in a low-intensity reflection in the direction of the detector when compared to the image of the laser spot on the retina. Thus it is ensured that an electronic observation of aiming and therapy laser without overexposure is possible despite the high radiation intensity of the laser. Thereby, it can be advantageous under certain circumstances to effect a decrease in intensity through filters in front of the detector.

In an additional advantageous embodiment, means for image processing and analysis as well as documentation and storage of the image and patient data are available. Thereto, the ophthalmological device exhibits oculars and/or a monitor and/or a display for online observation of the eye.

Preferably, a processing unit is available thereto, which supports the operator during processing also with regard to diagnostic statements and therapy planning. In addition, the processing unit is used for determining all control data and monitoring of the entire application.

In order to perform a diagnosis or therapy, the scan unit SE in the beam path for the scanning illumination is controlled by the control unit in such a way that the light of the second illumination source BQ is mapped through the pupil P of the eye onto the respective areas of the retina R.

Laser light focused on the retina, for example, with the aid of the emitted light of the tissue (backscatter, autofluorescence) or a fluorescence injected through contrast agents, allows for conclusive diagnoses. Alternatively, the laser light focused on the retina with sufficiently high energy density can also be used for therapeutic purposes, such as mechanical fixation of the retina or manipulation of metabolic processes.

Thereto it is advantageous if the intensity of the second illumination source can be diminished, allowing, in addition to photocoagulation, also for other types of laser therapy, e.g., biostimulation through local warming of areas of the retina.

Thereto, the use of a wide field illumination is advantageous since the decoupling of diagnosis/therapy and imaging allows for online monitoring of the diagnostic and/or therapeutic processes. As a result, permanent control of the position of the laser spot on the retina is possible during diagnosis and therapy. Moreover, it is possible to monitor the optical reaction of the activated laser spot on the retina, determine the corresponding measured value and to prompt the deactivation of the illumination source when a predetermined threshold value is reached.

In an additional advantageous embodiment, the second illumination source can be used for projecting light in the form of a marker into the eye. This allows for a targeted alignment of the patient's line of vision through fixation of the eye onto said marker in order to examine peripheral areas of the eye.

An additional advantageous embodiment is achieved through projecting temporally and locally variable light markers and/or indicator fields into the eye from the second illumination source; their perceptibility will be confirmed by the patient via appropriate means. As a result, the ophthalmological device, according to the invention, can even be used for perimetric examination, i.e., for determining the field of view of the patient. Thereto, the data of the temporally and locally variable light markers and/or indicator fields as well as the patient's confirmed/non-confirmed perceptibility are documented and stored.

Thereto, with a wide field illumination (first illumination source), markers (second illumination source) with variable XY deflection are projected onto the retina. Thereby, the spots advantageously exhibit different geometries, such as crosses, rings, points, and the like, at various intensities (from few μW up to threshold values for class 1 lasers) as well as temporal modulation (e.g., blinking with various pulse widths and frequencies).

The patient's subjective feedback regarding the perceptibility of the markers, e.g., through the touch of a button, is recorded, documented and analyzed.

Once again, the use of a wide field illumination allows for a permanent control of the position of the markers on the retina during the perimetric examination. Through online monitoring by the operator, a simple test of the plausibility of the feedback of the recognizability by the patient is possible.

In an additional advantageous embodiment, the configuration, according to the invention, can be used for fluorescence imaging of the eye.

The fluorescence excitation in the eye is achieved by application of the second illumination source which, for said purpose, emits an ultraviolet, visible, or infrared spectrum. Then the fluorescence signals initiated in the eye are, preferably, recorded by a wavelength-selective detector.

Thereby, the use of a laser, which emits ultrashort pulses, as illumination source for the scanning illumination proves particularly advantageous. Once again, the fluorescence excitation in the eye is achieved by means of an ultraviolet, visible, or infrared spectrum, whereby the pulse widths are in the range of ns, ps, or fs. However, in this case, a temporally high-definition detector, for example, a detector operating in accordance with the TCSPS principle (time-correlated single photon counting), is used for the recording of the fluorescence initiated in the eye. With this special embodiment of the configuration, according to the invention, it is possible to execute a fluorescence lifetime imaging of the eye.

An additional advantageous embodiment of the ophthalmological device for observation, examination, diagnosis, and/or therapy of an eye offers, on the one hand, the use of an aiming laser, which is followed by the treatment laser during treatment (diagnosis or therapy). This allows for an easier observation of the treatment. On the other hand, the movement of the retina can be monitored with the use of an eye tracker, hence avoiding treatment errors due to movement of the eye. With an eye tracker, the position of the eye as well as its alignment (line of vision) can be monitored.

In the method for observation, examination, diagnosis, and/or therapy of an eye, according to the invention, the eye is illuminated for observation and examination by a first illumination source via an existing perforated mirror and imaging optics, and the light emitted from the eye is mapped onto a detector via imaging optics and through the perforated mirror.

For diagnosis and/or therapy, the eye is additionally illuminated with a second illumination source via a scan unit, a lens, a beam splitter, and imaging optics, whereby the scan unit in the form of one or several bidirectionally adjustable mirrors is driven electrostatically and/or galvanometrically. The imaging optics as well as the entire beam path are designed in such a way that no internal reflections occur.

The non-reflective design of the entire beam path and, particularly, the imaging optics, is an important requirement for the function of the suggested technical solution; otherwise, laser light reflected in the imaging optics would outshine the illumination used for imaging on the camera.

For diagnosis and/or therapy it is hereby particularly advantageous that the scan unit is quasistatically driven and designed in the form of one bidirectional or two unidirectional, electrostatically and/or galvanometrically driven adjustable mirrors in MEMS technology. As a result, the scan unit is capable of correcting lateral chromatic aberrations of the laser light source and/or the imaging optics. Thereby, said correction can, preferably, take place sequentially for different wavelengths. An additional option for correcting lateral chromatic aberrations of the imaging optics, and therefore the position of the laser spots of different wavelengths on the retina, is the use of a chromatically pre-corrected scan lens. As a result, the position of the laser spot on the retina can be ensured with high reproducibility even with different laser wavelengths, especially in case of optical imaging aberrations.

Moreover, an existing defective vision of the eye can be compensated in such a way that at least one optical component is arranged adjustably in the beam path for the scanning illumination. This can either be the lens positioned in the beam path for the scanning illumination or the existing collimation optics for the collimation of the laser on the scan unit.

If several lasers are used, one or several collimation optics can thereby be adjustable. Thereby, it is ensured that despite existing defective vision, a precisely accurate image of the laser spot on the retina is achieved. Thereto, the defective vision is preferably determined automatically by the ophthalmological device, similar to a fundus camera, with the values for sphere and, optionally, also for cylinder and/or the higher-order aberrations and then taken into consideration for the imaging of the laser on the retina.

In order to optimize the second illumination source for the various tasks during observation and examination and/or diagnosis and/or therapy treatment of the eye, said illumination source is capable of mapping spots or even markers onto the retina, which vary with regard to form, wavelength, intensity as well as pulse duration and repetition, and monitoring the threshold values.

If said threshold value is reached and/or other unforeseeable events occur, the diagnosis and/or therapy can be interrupted by the control unit through deactivation of the laser source via different safety-relevant components. In addition, the control unit also monitors the position of the laser spot on the retina in order to reduce possible cases of error to an infinitesimal minimum.

Thereby, the existing safety mechanisms must function with such accuracy and speed that especially the laser energy of aiming and therapy beam is reduced to a non-critical minimum in case of error. Furthermore, the existing safety mechanisms should function independently from each other as well as from possible operational errors by the operator.

The coupling of the scanning illumination is an additional essential procedural step, according to the invention. Thereto, the existing dichroitic or polarization-dependent beam splitter in the beam path for the scanning illumination is arranged in such a way that the second illumination source is mapped centrally in the eye pupil via the scan unit and the lens.

As already described, during the ophthalmological method, according to the invention, the light, originating from a first illumination source, is mapped via a perforated mirror and imaging optics through the pupil on the retina of the eye, and for the purpose of imaging, the light reflected from the retina of the eye is mapped on a detector through the pupil of the eye via the imaging optics while forming an intermediate image through the aperture of the perforated mirror. Commonly, a CCD camera or CMOS camera is once again used as detector. In addition to this method, the light of a second illumination source is mapped on the retina of the eye for the diagnosis, and/or therapy of an eye via a scan unit, a lens, and a beam splitter. Thereby, the dichroitic or polarization-dependent beam splitter is arranged in such a way that the light from the second illumination source is mapped centrally in the pupil of the eye. Thereby, the second illumination source consists of at least one but preferably several laser sources, the collimated beams of which are coupled via the beam splitter before the scan unit and the lens into the beam path for the scanning illumination.

The movement of the scan unit and the connected change of the deflection angle of the light correspond to a change of angle of the light in the pupil of the eye and, therefore, to a change of position of the light spot on the retina. Thereby, the conditions of the laser during entry into the eye, such as beam diameter and numerical aperture on the cornea, correspond to those at the exit of a contact glass with the use of a slit lamp, and under which the therapeutic procedure on the retina are executed. Contrarily, however, no contact glass is used for compensating the refractive power of the eye.

The diagnostic and/or therapeutic use of a laser requires the free positionability of the laser spot on the retina within the accessible scan area. Due to the imaging of the scan unit in the pupil of the eye, it is advantageous to insert a single scan mirror. An electrostatically and/or galvanometrically driven bidirectionally adjustable mirror designed with MEMS technology can advantageously be tilted on two axis around a pivot point during the quasistatic operation. Alternatively, two unidirectionally adjustable mirrors can be used as scan unit. Thereby, it is advantageous to map the first adjustable mirror by means of intermediate optics on the second adjustable mirror, otherwise the subsequent image of the scan unit can at best only take place optimally for one of the mirrors. With an electrostatic drive with direct current U, the adjustable mirrors posses the ability of tilting around an appropriately proportional angle $\theta$ and to keep such position until the value of the direct current U changes. In case of a galvanometric drive, the mirror is deflected statically around a current-proportional angle $\theta$ by means of direct current I, which runs through a coil connected with the mirror. This allows for a defined static positioning of the diffracted laser.

With the method, according to the invention, it is also possible to scanningly project several single light beams of the second illumination source simultaneously onto the eye. Thereto, the second illumination source consists of several single light sources in the form of laser light sources, the single beams of which are coupled via beam splitter and collimation optics into the beam path for the scanning illumination and simultaneously projected into the eye via the scan unit.

This ensures that the image of the scan unit, i.e. all laser light beams mapped simultaneously in that location, is projected scanningly into the pupil of the eye.

For example, said variation of the configuration can, aside from a therapy or excitation beam for fluorescence examinations or the like, be used to project an additional aiming beam within the visible spectral range into the eye.

It has a beneficial effect that the light beams of both illumination sources are widened at the optical boundary layers of the eye, resulting in a low-intensity reflection in the direction of the detector when compared to the image of the laser spot on the retina. Thus it is ensured that an electronic observation of aiming and therapy laser without overexposure is possible despite the high radiation intensity of the laser.

It is advisable for observation and examination as well as treatment to process, analyze, document, and together with patient data, store the images taken by the detector. Preferably, a processing unit is used thereto, which supports the operator during processing also with regard to diagnostic statements and therapy planning. Furthermore, the processing unit is used for determining all control data and monitoring of the entire application. In addition to the processing unit, oculars and/or a monitor and/or a display for online observation of the eye are available.

In order to perform diagnosis or therapy, the scan unit in the beam path for the scanning illumination is controlled by the control unit in such a way that the light of the second illumination source is mapped through the pupil of the eye onto the respective areas of the retina.

Laser light focused on the retina, for example, with the aid of the emitted light of the tissue (backscatter, autofluorescence) or a fluorescence injected through contrast agents, allows for conclusive diagnoses. Alternatively, the laser light focused on the retina with sufficiently high energy density can also be used for therapeutic purposes, such as mechanical fixation of the retina or manipulation of metabolic processes.

Thereto, it is advantageous if the intensity of the second illumination source can be diminished, allowing, in addition to photocoagulation, also for other types of laser therapy, e.g., biostimulation through local warming of areas of the retina.

Thereto, the use of a wide field illumination is advantageous since the decoupling of diagnosis/therapy and imaging allows for online monitoring of the diagnostic and/or therapeutic processes. As a result, permanent control of the position of the laser spot on the retina is possible during diagnosis and therapy. Moreover, it is possible to monitor the optical reaction of the activated laser spot on the retina, determine the corresponding measured value and to prompt the deactivation of the illumination source when a predetermined threshold value is reached.

The method, according to the invention, can also be used for the targeted alignment of the patient's line of vision if light in the form of a marker is projected into the eye from the second illumination source, which is used by the patient for aligning his/her line of vision. Through fixation of the eye onto said marker, it is possible to examine peripheral areas of the eye.

An additional advantageous embodiment is achieved, when temporally and locally variable light markers and/or indicator fields are projected into the eye from the second illumination source; their perceptibility will be confirmed by the patient via appropriate means. As a result, the ophthalmological method, according to the invention, can even be used for perimetric examination, i.e., for determining the vision field of the patient. Thereto, the data of the temporally and locally variable light markers and/or indicator fields as well as the patient's confirmed/non-confirmed perceptibility are documented and stored.

Thereto, with a wide field illumination (first illumination source), markers (second illumination source) with variable XY deflection are projected onto the retina. Thereby, the spots advantageously exhibit different geometries, such as crosses, rings, points, and the like, at various intensities (from few μW up to threshold values for class 1 lasers) as well as temporal modulation (e.g., blinking with various pulse widths and frequencies) and different wavelengths (ultraviolet, visible, and infrared light).

Optionally, the fundus can be illuminated by means of the wide field illumination (first light source) with special wavelengths.

An additional advantageous embodiment is the patient's line of vision with an internal fixation target in order to examine, e.g., the peripheral areas of the eye.

The patient's subjective feedback regarding the perceptibility of the markers, e.g., through the touch of a button, is recorded, documented, and analyzed.

Once again, the use of a wide field illumination allows for a permanent control of the position of the markers on the retina during the perimetric examination. Through online monitoring by the operator, a simple test of the plausibility of the feedback of the recognizability by the patient and, if necessary, an adjustment of the stimulus with regard to geometry, intensity, wavelength, and temporal modulation is possible.

An additional advantageous embodiment of the ophthalmological device for observation, examination, diagnosis, and/or therapy of an eye offers, on the one hand, the use of an aiming laser, which is followed by the treatment laser during treatment (diagnosis or therapy). This allows for an easier observation of the treatment.

On the other hand, the movement of the retina can be monitored with the use of an eye tracker, hence avoiding treatment errors due to movement of the eye. With an eye tracker, the position of the eye as well as its alignment (line of vision) can be monitored.

The following description shall describe briefly and by way of example, the method for observation, examination, diagnosis, and/or therapy of an eye, according to the invention, and document the diversity of its variations and broad range of applications.

After the eye to be examined and/or treated is brought into a defined position at the beginning of the procedure, one or several pictures are taken of the fundus at various illumination conditions in order to allow for as precise a diagnosis as possible. As described before, already existing fundus images, which are stored in the device and were taken at an earlier date or which originate from a different ophthalmological device, can optionally be used for diagnostic purposes.

Subsequently, i.e., after analysis of the fundus images, a therapy plan is prepared on the basis of the diagnosis at hand. In particular, the positions of the laser spots to be applied on the retina as well as the parameter for the therapy laser, such as wavelength, energy, pulse duration, pulse repetition, spot profile, and spot diameter, are determined.

With a comprehensive application of the laser spots, it is possible to mark the area to be treated and to automatically generate a treatment pattern of laser spots. Furthermore, it is possible, with a variety of laser spots to be applied, to optimize the sequence of the positioning regarding minimal setting time of the adjustable mirrors.

By determining the positions and the parameters for the therapy laser, the control data for the MEMS mirror, observation and imaging, as well as the data for the safety devices, are generated. If an aiming beam is to be used, the necessary data thereto will also be generated. Advantageously, the defective vision of the eye to be treated can also be taken into consideration.

After triggering the therapy, all relevant therapy data is monitored and documented online during the entire treatment, i.e., in case of existing deviations between therapy presets and treatment results, an immediate termination can be initiated. After therapy is concluded, all therapy data, particularly the spot positions on the retina, are documented with the corresponding laser data.

The solution, according to the invention, provides an ophthalmological device and method, with which not only observations and examinations, but also diagnoses and/or therapies of an eye are possible.

In an additional advantageous embodiment, the configuration, according to the invention, can be used for fluorescence imaging of the eye. The fluorescence excitation in the eye is achieved by means of the second illumination source which, for said purpose, emits an ultraviolet, visible, or infrared spectrum. Then the fluorescence signals initiated in the eye are, preferably, recorded by a wavelength-selective detector.

Thereby, the use of a laser, which emits ultrashort pulses, as illumination source for the scanning illumination proves particularly advantageous. Once again, the fluorescence excitation in the eye is achieved by means of an ultraviolet, visible, or infrared spectrum, whereby the pulse widths are in the range of ns, ps, or fs.

However, in this case, a temporally high-definition detector, for example, a detector operating in accordance with the TCSPC principle (time-correlated single photon counting), is used for the recording of the fluorescence initiated in the eye. With this special embodiment of the configuration, according to the invention, it is possible to execute a fluorescence lifetime imaging of the eye.

Moreover, the suggested solution offers the option of online monitoring and documentation of the therapy progress, improving and simplifying the evaluation of the therapeutic success.

The completely non-contact approach is particularly advantageous since the risk of infections and the like no longer exists.

Compared to prior art, the suggested solution offers the advantages that the physician now has the option through online monitoring and, especially, through the online retina image, to directly adjust treatment. For example, in a perimetric examination, the plausibility of the patient-confirmed recognizability of the markers can be confirmed. Adaptation of the markers allows for a targeted microperimetry in medically noticeable areas of the retina, whereby the physician can check and/or change the marker at any time. For further improvement of the perimetric examination, the marker can be adaptively adjusted by the physician with regard to intensity, geometry, or wavelength.

The ophthalmological device for observation, examination, diagnosis, and/or therapy of an eye also offers the possibility of combining any diagnostic and therapeutic procedures since a diagnosis and therapy plan can be rendered at any given time. Thereto, prior diagnostic and therapeutic data can be reviewed and new fundus images be created.

For example, spectral analyses of the light remitted from the fundus can be performed in combination with a diffractive and/or refractive spectrometer as well as a suitable detector (photodiode, CCD camera) or an interferometer. Thereto, spectrometer, detector as well as interferometer, can be incorporated in the described beam path either via the existing observation beam path or the scan unit.

Furthermore, such a structure allows for coherence tomography in order to gather depth information about the tissue of the retina. By means of laser polarimetry, the thickness of periodically arranged structures on the eye fundus (such as nerve fibers) can be determined. Thereto, as a second light source, a laser is coupled via the scan unit into the beam path by means of a defined polarization plane.

A double refraction of the laser light is caused by a regular structure on and/or in the retina. Thereby, the occurring phase shift of both refracted components is therefore a measure for the thickness of the regularly arranged structure. Through compensation of the double refraction, information regarding regular structures of the retina can be gathered for each patient individually. The advantages hereby are the permanent monitoring by the physician (by means of the retina image) as well as the very rapid local change of the laser spot through which individual changes in medically noticeable areas of the retina can directly be determined.

In combination with adaptive optical elements (membrane mirror, spatial light modulator), individual eye defects can be determined and corrected, and/or general optical defects in the observation beam path can be corrected.

The advantage of the applied scan unit in the form of a single electrostatically and/or galvanometrically driven bidirectionally adjustable mirror designed with MEMS technology and quasistatically driven is based on the beam deflection, which takes place, preferably simultaneously, in directions x and y, whereby the beam path is mapped precisely in the system aperture, i.e., the human iris.

LEGEND

R Retina
P Pupil
AO Imaging optics
Z Intermediate image
LS Perforated mirror
D Detector
BQ Illumination source
BL Illumination light
LQ Laser source
LL Laser light
KO Collimation optics
SE Scan unit
KS Adjustable mirror
O Lens
ST Beam splitter

The invention claimed is:

1. An ophthalmological device for observation, examination, diagnosis, and/or therapy of an eye, comprising:
    an illumination beam path which, originating from a first illumination source, leads to the eye, and includes a perforated mirror and imaging optics;
    an observation beam path, which, originating from the retina of the eye, leads via the imaging optics and through the perforated mirror to a detector;
    a beam path for scanning illumination, which, originating from a laser source, leads to the retina of the eye, and, in addition to the imaging optics, includes a scan unit, a lens, and a beam splitter, and wherein the imaging optics and the entire beam path are designed such that they are free of internal reflections, and the scan unit comprises a single electrostatically and/or galvanometrically driven, bi-directionally adjustable mirror or several electrostatically and/or galvanometrically driven, unidirectionally adjustable mirrors.

2. The device according to claim 1, wherein the scan unit, having electrostatically and/or galvanometrically driven, unidirectionally or bi-directionally adjustable mirrors, comprises MEMS technology and is used for quasistatic operation.

3. The device according to claim 1, wherein the scan unit, comprising MEMS technology, corrects for lateral chromatic aberrations of the laser source.

4. The device according to claim 1, wherein the lens, positioned in the beam path for the scanning illumination, and/or collimation optics for the collimation of laser light of the laser source on the scan unit are adjustable to compensate for defective vision of the eye.

5. The device according to claim 1, further comprising structure for projecting markers from the laser source into the eye as well as their variations with regard to form, wavelength, intensity as well as pulse duration and repetition.

6. The device according to claim 1, further comprising a control unit programmed to vary the light emitted by the illumination light source with regard to form, wavelength, intensity, as well as pulse duration and repetition and for monitoring their threshold values.

7. The device according to claim 1, wherein the laser source comprises several single light sources in the form of laser light sources, a beam splitter and collimation optics for possible simultaneous coupling of laser light in the beam path for the scanning illumination before the scan unit.

8. The device according to claim 1, wherein the laser source emits an ultraviolet, visible, or infrared wavelength for fluorescence excitation in the eye, and wherein the detector comprises a wavelength-selective detector for recording correlated fluorescence signals from the eye.

9. The device according to claim 1, wherein the laser source for the scanning illumination is a laser, which emits ultra short pulses, and wherein the detector comprises a temporally high-definition detector for recording the correlated fluorescence signals of the eye.

10. The device according to claim 1, wherein the beam splitter comprises a dichroitic or polarization-dependent beam splitter in the beam path for the scanning illumination and the beam splitter is arranged such that the laser source is mapped centrally in the pupil of the eye via the scan unit and the lens.

11. The device according to claim 1, further comprising a device for image processing and analysis and for documentation and storage of image and patient data.

12. The device according to claim 1, further comprising oculars, a monitor or a display to observe the eye.

13. The device according to claim 1, wherein the scan unit scans laser light for diagnosis and/or therapy via the beam path and is controlled by the control unit such that the laser light is mapped through the pupil of the eye onto selected areas of the retina.

14. The device according to claim 1, wherein laser light in the form of a marker, projected into the eye from the laser source, is presented for targeted alignment of the line of vision through fixation of the eye onto said marker.

15. The device according to claim 1, further comprising a device to register a patient's response regarding the perceptibility of the light, projected into the eye from the laser source in the form of temporally and locally variable light markers and/or indicator fields, and a device that documents and stores data related to the patient's responses to determine a visual field of the patient.

16. The method according to claim 15, further comprising structuring the laser source such that the laser source emits an ultraviolet, visible, or infrared spectrum for fluorescence excitation in the eye; and
   detecting correlated fluorescence signals of the eye by a wavelength-selective detector.

17. A method for observation, examination, diagnosis, and/or therapy of an eye, comprising:
   illuminating the eye for observation and examination by a first illumination source via a perforated mirror and imaging optics;
   illuminating the eye, for diagnosis and/or therapy with a laser source via a scan unit, a lens, a beam splitter, and the imaging optics;
   mapping light returned from the eye onto a detector via the imaging optics and through the perforated mirror;
   structuring the imaging optics and a beam path such that no internal reflections occur; and
   structuring the scan unit to be in the form of an adjustable mirror driven electrostatically and/or galvanometrically and bi-directionally, or to be in the form of several adjustable mirrors driven electrostatically and/or galvanometrically and unidirectionally.

18. The method according to claim 17, further comprising designing the scan unit in the form of one electrostatically and/or galvanometrically driven mirror that is bi-directionally moved, or several unidirectionally moved, adjustable mirrors using MEMS technology, and designing the mirror or mirrors to be driven quasistatically.

19. The method, according to claim 17, further comprising correcting lateral chromatic aberrations of the laser source with the scan unit that is designed according to MEMS technology.

20. The method according to claim 17, further comprising making the lens, positioned in the beam path for the scanning illumination, and/or collimation optics for collimation of laser light from the laser source on the scan unit adjustable for compensation of defective vision of the eye.

21. The method according to claim 17, further comprising structuring the laser source to include at least one laser light source for depicting markers that can be varied with regard to form, wavelength, intensity as well as pulse duration and repetition.

22. The method according to claim 17, further comprising using a control unit to vary the light emitted by the illumination light source with regard to form, wavelength, intensity as well as pulse duration and repetition, and using the control unit to monitor threshold values.

23. The method according to claim 17, further comprising structuring the laser source to include several single light sources in the form of laser light sources;
   coupling the laser light of the laser light sources via a beam splitter and collimation optics into the beam path for the scanning illumination; and
   simultaneously projecting the laser light into the eye via the scan unit.

24. The method according to claim 17, further comprising structuring the laser source to emits ultra short pulses; and
   detecting correlated fluorescence signals from the eye by a temporally high-definition detector.

25. The method according to claim 17, further comprising structuring the beam splitter positioned in the beam path for the scanning illumination between imaging optics and perforated mirror to be dichroitic or polarization-dependent; and
   mapping the laser source via the scan unit and the lens centrally in the pupil of the eye.

26. The method according to claim 17, further comprising processing, analyzing, documenting, and storing images recorded by the detector together with patient data.

27. The method according to claim 17, further comprising observing the eye via oculars, a monitor or a display.

28. The method according to claim 17, further comprising controlling the scan unit such that laser light for diagnosis and/or therapy from the laser source in the beam path is mapped through the pupil of the eye onto the selected areas of the retina.

29. The method according to claim 17 further comprising projecting laser light in the form of a marker, into the eye for targeted alignment of the patient's line of vision through fixation of the eye onto said marker.

30. The method according to claim 17, further comprising projecting laser light from the laser source in the form of temporally and locally variable light markers and/or indicator fields into the eye;
   registering a patient's response regarding the perceptibility of the light; and
   documenting and storing data related to the patient's responses to determine a visual field of the patient.

* * * * *

UNITED STATES PATENT AND TRADEMARK OFFICE
CERTIFICATE OF CORRECTION

PATENT NO. : 8,123,353 B2
APPLICATION NO. : 12/919478
DATED : February 28, 2012
INVENTOR(S) : Detlef Biernat et al.

Page 1 of 1

It is certified that error appears in the above-identified patent and that said Letters Patent is hereby corrected as shown below:

In the Specifications

Col. 1, line 60, delete "photo coagulation of by application" insert -- photo coagulation or by application --.

Col. 2, line 61, delete "scanning imaging of the fundus" insert -- scanning/imaging of the fundus --.

Col. 6, line 51, delete "aberrations, and taken into consideration" insert -- aberrations, taken into consideration --.

Col. 8, line 36, delete "can also includes more" insert -- can also include more --.

Col. 11, line 67, delete "be used as scan unit" insert -- be used as the scan unit --.

In the Claims

Col. 18, line 24, Claim 24, delete "laser source to emits ultra short pulses" insert -- laser source to emit ultra short pulses --.

Signed and Sealed this
Fourteenth Day of May, 2013

Teresa Stanek Rea
*Acting Director of the United States Patent and Trademark Office*